United States Patent [19]

Tokizawa et al.

[11] Patent Number: 5,147,886
[45] Date of Patent: Sep. 15, 1992

[54] TRIAZOLE DERIVATIVES AND A COMPOSITION FOR TREATING MYCOSES

[75] Inventors: Minoru Tokizawa; Yoshihiko Kanamaru, both of Narita; Masaru Matsumoto, Tomisato; Takemitsu Asaoka, Narita; Hideaki Matsuda, Abiko; Tadayuki Kuraishi, Chiba; Kazunori Maebashi, Narashino; Naokata Taido, Funabashi; Ryuichi Kawahara, Ichikawa, all of Japan

[73] Assignee: SS Pharmaceutical Co., Ltd., Tokyo, Japan

[21] Appl. No.: 626,545

[22] Filed: Dec. 12, 1990

[30] Foreign Application Priority Data

Dec. 25, 1989 [JP] Japan .................. 1-335946
Oct. 9, 1990 [JP] Japan .................. 2-270783

[51] Int. Cl.$^5$ .................. A61K 31/41; C07D 249/08
[52] U.S. Cl. .................. 514/383; 548/268.6
[58] Field of Search .................. 548/268.6; 514/383

[56] References Cited

U.S. PATENT DOCUMENTS 4,661,507 4/1987 Gymer et al. .................. 548/268.6
5,004,494 4/1991 Sugavanam et al. .................. 548/268.6

FOREIGN PATENT DOCUMENTS 086173 8/1983 European Pat. Off. .......... 548/268.6
2103210 2/1983 United Kingdom .......... 548/268.6

Primary Examiner—Patricia L. Morris
Attorney, Agent, or Firm—Oblon, Spivak, McClelland, Maier & Neustadt

[57] ABSTRACT

A triazole derivative is disclosed. The compound have a general formula,

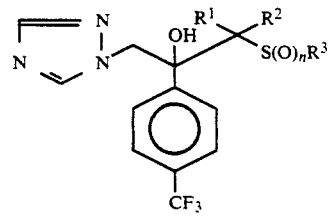

wherein $R^1$ and $R^2$ represent a hydrogen atom or a lower alkyl group, or $R^1$ and $R^2$ together form a lower alkylene group, $R^3$ represents a lower alkyl group, and n denotes an integer of 0 to 2, provided that not both $R^1$ and $R^2$ are a hydrogen atom at the same time. The triazole derivatives and their salts are effective for curing or preventing deep-seated mycoses, e.g. mycotic meningitis, mycotic infectious diseases of respiratory organs, fungemia, and urinary tract mycosis.

2 Claims, No Drawings

TRIAZOLE DERIVATIVES AND A COMPOSITION FOR TREATING MYCOSES

BACKGROUND OF THE INVENTION

Field of the Invention

This invention relates to novel triazole derivatives and salts thereof possessing excellent antimycotic activity and to a composition for curing mycoses comprising the same.

Description of the Background Arts

Mycosis is classified into skin diseases typified by trichophytosis, psoriasis, skin candidasis, and the like and deep-seated mycoses which include mycotic meningitis, mycotic infectious diseases of respiratory organs, fungemia, urinary tract mycosis, and the like.

Of these, patients of deep-seated mycoses are increasing, since they cannot be cured by conventional antibiotics or chemotherapic agents. Development of a drug efficacious for the treatment of these diseases has therefore been desired.

Very few drugs for curing deep mycoses are known. Only ketoconazole, fluconazole, and the like among azole compounds have been known as drugs for curing deep-seated mycoses. Their effects, however, are not necessarily satisfactory.

SUMMARY OF THE INVENTION

In view of this situation, the present inventors have synthesized a number of triazole compounds and studied their antimycotic activities, and have found that triazole derivatives having the following formula (I) exhibited excellent antimycotic activity.

Accordingly, an object of the present invention is to provide a triazole derivative of formula (I),

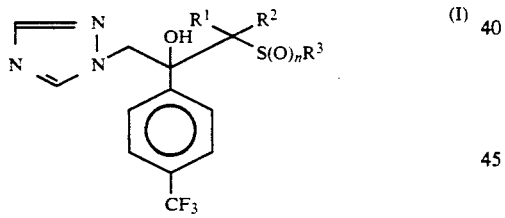

wherein $R^1$ and $R^2$ represent a hydrogen atom or a lower alkyl group, or $R^1$ and $R^2$ together form a lower alkylene group, $R^3$ represents a lower alkyl group, and n denotes an integer of 0 to 2, provided that $R^1$ and $R^2$ are not both a hydrogen atom at the same time, and a salt thereof; and a composition for curing mycoses comprising such a triazole derivative or a salt thereof.

Other objects, features and advantages of the invention will hereinafter become more readily apparent from the following description.

DETAILED DESCRIPTION OF THE INVENTION AND PREFERRED EMBODIMENTS

A lower alkyl group represented by $R^1$, $R^2$, and $R^3$ in formula (I) is a linear or branched alkyl group having 1 to 6 carbon atoms. Specific examples are methyl-, ethyl-, n-propyl-, isopropyl-, n-butyl-, isobutyl-, sec-butyl-, tert-butyl-, n-pentyl-, and n-hexyl groups. A lower alkylene group which $R^1$ and $R^2$ form in combination is, for example, ethylene-, trimethylene-, or tetramethylene group.

Hydrochloride, nitrate, hydrobromide, sulfate, p-toluenesulfonate, methanesulfonate, fumarate, maleate, succinate, lactate, and the like are given as examples of the salts of the compound of formula (I).

There are optical isomers due to the asymmetric carbon atom and sulfur atom for the compound of formula (I). All of racemates, optical active isomers, and diasteromers are included in this invention.

Triazole derivatives of formula (I) and their salts can be prepared, for example, according to the following reactions.

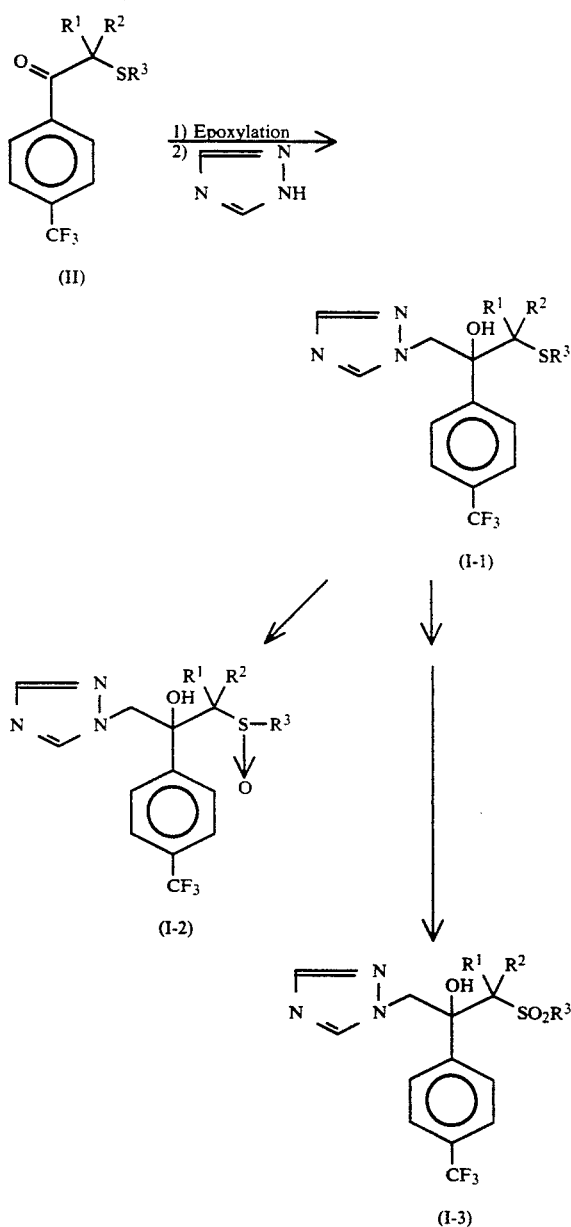

wherein $R^1$, $R^2$, and $R^3$ have the same meanings as defined above.

First, compound (II) is epoxylated and reacted with triazole to produce sulfide compound (I-1). The sulfide compound (I-1) is then oxidized to obtain sulfinyl compound (I-2) or sulfonyl compound (I-3). Each step is described in more detail below.

The reaction to produce sulfide compound (I-1) from compound (II) is preferably carried out by using 1 to 2 moles of epoxylation agent, e.g. trimethylsulfoxonium iodide, and 1 to 3 moles of triazole for 1 mole of compound (II) in the presence of 2 to 5 moles of an alkali compound and by heating the mixture at room temperature to 100° C. for 1 to 30 hours. Sodium hydroxide, potassium hydroxide, barium hydroxide, sodium carbonate, potassium carbonate, or the like can be used as an alkali. Of these, alkali hydroxides are particularly preferable. An alcohol such as methanol, ethanol, propanol, isopropanol, butanol, isobutanol, sec-butanol, tert-butanol, or the like is used as a solvent.

After completion of the reaction, the organic solvent is evaporated, ice-cooled water is added to the residue, and the residue is extracted with a solvent such as chloroform or the like. The target compound can be obtained by drying the chloroform layer, evaporating the solvent, and purifying by silica gel column chromatography or the like means.

When the sulfide compound (I-1) has different substituents; i.e., different $R^1$ and $R^2$, two types of diastereomers are produced; A isomer fractionated first by silica gel chromatography and B isomer which elutes later from the column.

The reaction for producing sulfinyl compound (I-2) from sulfide compound (I-1) is carried out by using 1 mole of oxidizing agent for 1 mole of sulfide compound (I-1) and by reacting at $-10°$ C. to room temperature for 0.1 to 2 hours. Organic peroxide, manganese dioxide, chromic acid, hydrogen peroxide, or the like can be used as the oxide for the reaction, with particularly preferable oxides being organic peroxides. A halogenated hydrocarbon is used as a preferable solvent. After completion of the reaction, the reaction mixture is washed with an alkali carbonate and then water, dried, distilled for removal of the solvent, and subjected to silica gel column chromatography for purification to obtain the target compound.

When the sulfinyl compound (I-2) has the same substituents $R^1$ and $R^2$, two types of diastereomers are produced; a isomer fractionated first by silica gel chromatography and b isomer which elutes later from the column. When $R^1$ and $R^2$ are different from each other, both a and b isomers are produced for each one of A and B isomers of sulfide compound (I-1).

The reaction for producing sulfonyl compound (I-3) from sulfide compound (I-1) is carried out by using 2 to 5 moles of oxidizing agent for 1 mole of sulfide compound (I-1) at room temperature to 50° C. for 1 to 30 hours. The same oxidizing agent, solvent, and purification method as those for producing sulfinyl compound (I-2) can be employed.

Two types of diastereomers are present for sulfonyl compound (I-3), when the substituents $R^1$ and $R^2$ are different. When either one of A or B isomer of sulfide compound (I-1) is used, only one of the diastereomers of sulfonyl compound (I-3) is produced.

When the carbon atom which have a hydroxyl group substituent in the compound of formula (I) is the only asymmetric atom, there are two optical isomers present due to this asymmetric atom. Such optical isomers can be produced, for example, by the following reactions.

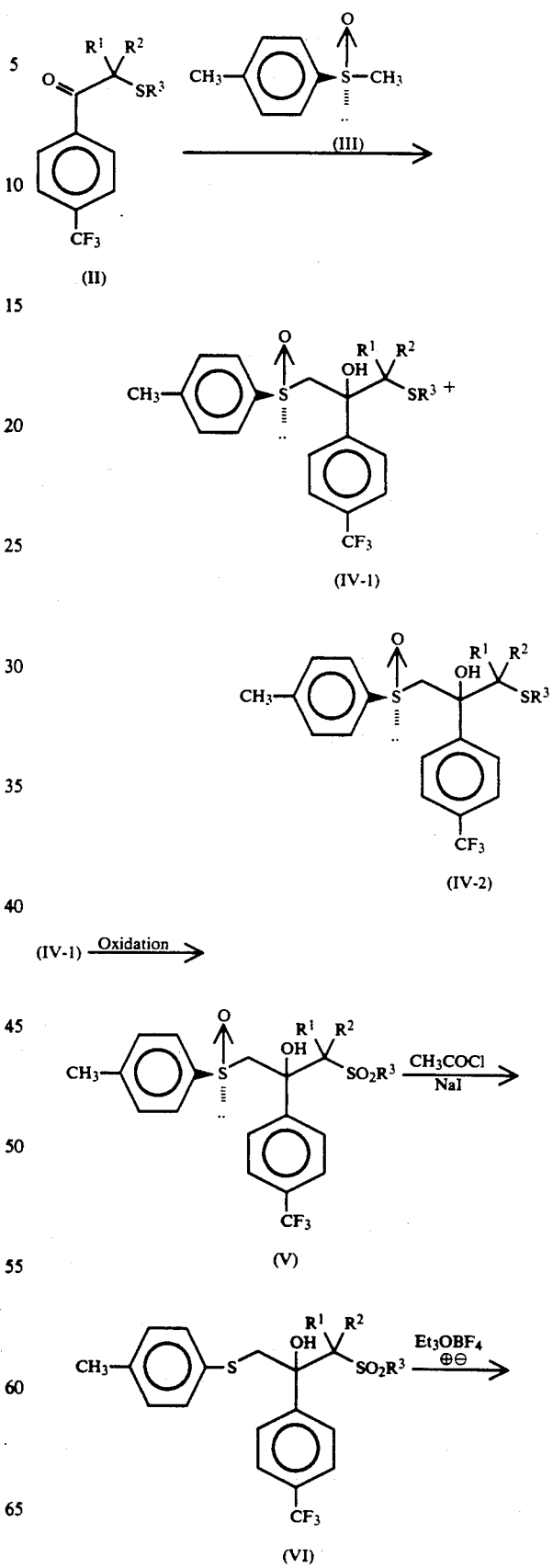

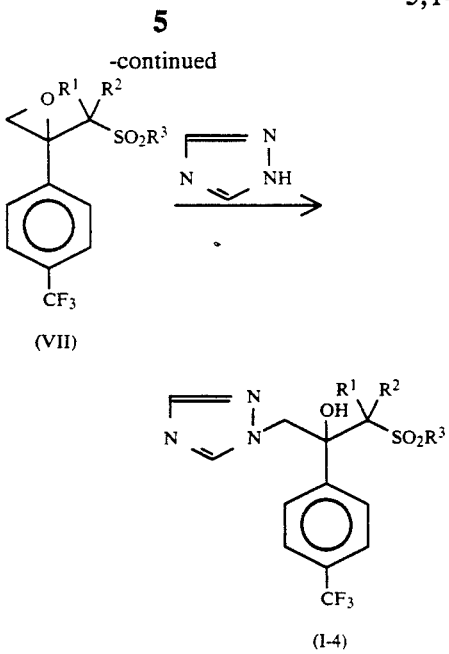

In the reaction scheme, $R^1$, $R^2$, and $R^3$ have the same meanings as defined above, and compounds (IV-1) and (IV-2) are diasteromers.

In the above reaction scheme, compound (II) is first reacted with optically active sulfinyl compound (III) to produce a mixture of diastereomers (IV-1) and (IV-2). Only one of the two diastereomers (IV-1) and (IV-2) is separated from the mixture and oxidized to produce sulfonyl compound (V). The sulfonyl compound (V) is then converted into compound (VI) by the reaction with acetyl chloride and sodium iodide. After epoxylation, the compound (VI) is reacted with triazole to obtain optically active compound (I-4).

Each of the above reactions are described in more detail.

Diastereomers (IV-1) and (IV-2) are produced by reacting 1 to 1.2 moles of optically active sulfinyl compound (III) for 1 mole of compound (II) in the presence of 1 to 1.4 moles of a base at 0° C. to room temperature for 0.5 to 5 hours. Ether, tetrahydrofuran, dioxane, n-hexane, or the like is used as a solvent. As a base, lithium diisopropylamide, butyl lithium, potassium t-butoxide, sodium amide, sodium hydride, calcium hydride, or the like can be used. Of these, a particularly preferable base is lithium diisopropylamide. In order to collect the target compound from the mixture containing two diastereomers, the reaction mixture is treated with ammonium chloride or the like, extracted with an organic solvent, and purified by silica gel column chromatography or the like. Purified diastereomer (VI-1) is thus obtained.

Diastereomer (VI-1) is then dissolved into a solvent such as chloroform, dichloromethane, or the like and to the solution 2 moles of an oxidizing agent is added for 1 mole of diastereomer (VI-1). The mixture is stirred at −10° C. to room temperature for 0.5 to 5 hours to obtain sulfonyl compound (V). Hydrogen peroxide, perbenzoic acid, m-chloroperbenzoic acid, or the like is used as an oxidizing agent. After the reaction, the reaction mixture is washed with an alkali and purified by silica gel column or the like to obtain sulfonyl compound (V).

Sulfonyl compound (V) thus obtained is dissolved into a solvent such as acetone and to the solution 1 to 3 moles of acetyl chloride and 1 to 3 moles of sodium iodide for 1 mole of sulfonyl compound (V) is added. The mixture is stirred at −10° C. to room temperature for 0.5 to 5 hours to obtain compound (VI). After the reaction, the reaction mixture is extracted with an organic solvent and purified by silica gel column or the like to obtain purified compound (VI).

Compound (VI) is dissolved into chloroform, dichloromethane, or the like, and to the solution is added 2 to 10 moles of triethyloxonium tetrafluoroborate for 1 mole of compound (VI). The mixture is stirred at 0° C. to room temperature for 10 to 30 hours to produce epoxylated compound (VII). After an addition of an alkali, the crude product is stirred at 0° C. to room temperature for 0.5 to 5 hours. The organic layer is submitted to silica gel column or the like to obtain purified epoxylated compound (VII).

Epoxylated compound (VII) is dissolved into a solvent such as N,N-dimethylformamide, dimethylsulfoxide, acetonitrile, t-butanol, or the like, and to the solution are added 1 to 10 moles of triazole and 1 to 10 moles of an alkali for 1 mole of compound (VII). The mixture is stirred at 0° C. to refluxing temperature for 1 to 30 hours to obtain the target optical active compound (I-4). Sodium hydroxide, potassium hydroxide, sodium carbonate, potassium carbonate, sodium bicarbonate, potassium bicarbonate, or the like can be used as an alkali. Purified optical active compound (I-4) can be obtained by extracting the reaction mixture with an organic solvent, evaporating the solvent, and recrystallizing from a suitable solvent.

The raw material compound (II) can easily be prepared according to the following reaction scheme (a) or (b). Reaction Scheme (a):

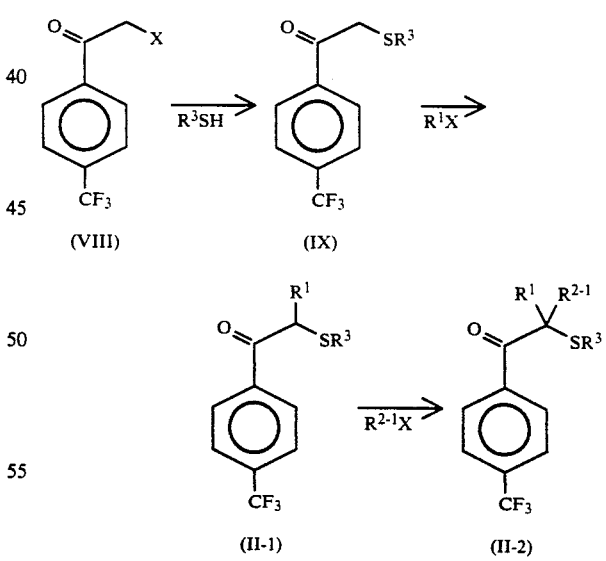

wherein X represents a halogen atom, $R^1$, $R^{2-1}$, and $R^3$ represent a lower alkyl group.

According to the reaction scheme (a), 4-(trifluoromethyl)phenacyl halide (VIII) is converted into the sulfide derivative (IX) by the treatment with a lower alkyl mercaptan in the presence of an alkali, followed by the reaction with a lower alkyl halide to produce monoalkyl derivative (II-1). If required, monoalkyl derivative (II-1) is further reacted with the lower alkyl halide to produce dialkyl derivative (II-2). Reaction Scheme (b):

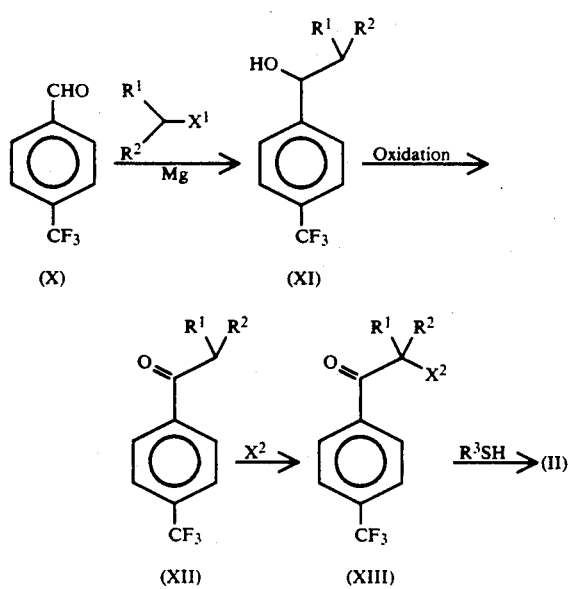

wherein $X^1$ and $X^2$ represent a halogen atom, $R^1$, $R^2$, and $R^3$ have the same meanings as defined previously.

According to the reaction scheme (b), 4-(trifluoromethyl)benzaldehyde (X) is converted into alcohol compound (XI) by the Grignard reaction, oxidized into ketone compound (XII), and successively halogenized into compound (XIII). Compound (XIII) is then reacted with mercaptan to obtain compound (II).

Antimycotic activity of compounds of formula (I) of the present invention is described by way of the following experiment.

Groups of ICR male mice (age: 4 weeks), each group consisting of 5 mice, were subjected to the experiment. $3.3 \times 10^6$ Candida albicans were injected into caudal vein of each mouse. Starting from 1 hour after the injection, test compounds dissolved in 0.5 ml of 0.06N hydrochloric acid solution to which 0.2% TO-10M (Trademark: product of Nikko Chemicals Co.) was added were orally administered once each day, four times in total. The mice were observed for 14 days after the injection of Candida albicans cans to compare the average survival days of the mice to which the test compounds were administered with the average survival days of the control group. The indicator T/C (%) were determined according to the following equation.

$$T/C\ (\%) = \frac{\text{Average survival days of the mice to which the test compounds were administered}}{\text{Average survival days of the control}}$$

The results are presented in Table 1, in which Compound Nos. are the same as those given in Table 2 hereinafter.

TABLE 1

| Compound No. | Dose (mg/kg) | Survived animals/ tested animals | T/C (%) |
|---|---|---|---|
| 7 | 5 | 5/5 | 412 |
|  | 2.5 | 3/5 | 394 |
|  | 1.25 | 0/5 | 235 |
| 10 | 5 | 3/5 | 406 |
|  | 2.5 | 2/5 | 394 |

TABLE 1-continued

| Compound No. | Dose (mg/kg) | Survived animals/ tested animals | T/C (%) |
|---|---|---|---|
|  | 1.25 | 1/5 | 306 |
|  | 0.625 | 1/5 | 235 |
| 16 | 5 | 5/5 | 412 |
|  | 2.5 | 3/5 | 400 |
|  | 1.25 | 2/5 | 371 |
|  | 0.625 | 2/5 | 341 |
| Fluconazole (Comparative compound) | 5 | 2/5 | 300 |
|  | 2.5 | 1/5 | 312 |
|  | 1.25 | 1/5 | 271 |
|  | 0.625 | 0/5 | 141 |
| Control | — | 0/5 | 100 |

As demonstrated by the above results, in the oral administration compounds of formula (I) the present invention exhibited a superior survival rate; the in vivo antimycotic effect, over fluconazole, the comparative compound.

When the compound of formula (I) of this invention or a salt thereof is used as an antimycotic agent, it is preferably orally administered at a dose of 50 to 500 mg per day or parenterally at a dose of 10 to 200 mg per day, depending on the weight, the age, the sex, the physical conditions, or the symptom of the patient or the way of administration.

The compound of formula (I) can be formed into various preparations, such as tablets, granules, powders, capsules, suspensions, injections, suppositories, or other forms for external application, according to known methods. When solid preparations are produced, the compound of formula (I) is mixed with excipients, and as required, with binders, disintegrators, lubricants, coloring agents, sweetening agents, flavoring agents, fillers, coating agents, sugar-coating agents, and the like, and formed into preparations such as tablets, granules, powders, capsules, suppositories, or the like according to known methods. The compound of the present invention can be also prepared into preparations for injection by dissolving, suspending, or emulsifying it into an aqueous medium such as distilled water, or by making it into powder which is dissolvable when it is injected. Subcutaneous, intravenous, intra-arterial, intra-portal, intraperitoneal, or intramuscular injection is applicable.

As discussed above, the compound of the present invention possesses high antimycotic activity. In addition, it is easily absorbed by living bodies, exhibiting its superior bioavailability. Thus, the compound is useful for curing mycoses or preventing infectious diseases in human and animals.

Other features of the invention will become apparent in the course of the following description of the exemplary embodiments which are given for illustration of the invention and are not intended to be limiting thereof.

EXAMPLES

Reference Example 1

To 13.2 g of 2-bromo-4'-(trifluoromethyl)acetophenone dissolved in 40 ml of methanol was added under ice-cooling 34.6 g of a 15% aqueous solution of methyl mercaptan sodium salt. After the reaction at room temperature for 1 hour with stirring, the resultant reaction mixture was poured into ice-cooled water and extracted with dichloromethane. The organic layer was washed with water and dried over anhydrous magnesium sulfate, followed by evaporation of the solvent to obtain 11.3 g of oily product of 2-methylthio-4'-(trifluoromethyl)acetophenone (yield: 97.7%).

NMR(CDC$_3$)δ: 2.13 (s, 3H), 3.77 (s, 2H), 7.74(d, 2H), 8.17(d, 2H)

Reference Example 2

To 5.00 g of 2-methylthio-4'-(trifluoromethyl)acetophenone dissolved in 50 ml of tetrahydrofuran was added under ice-cooling 0.855 g of a 60% aqueous solution of sodium hydride, and the mixture was reacted at room temperature with stirring until no bubbles were produced. After an addition of 3.34 g of methyl iodide, the mixture was stirred at room temperature for a further 2 hours. The resultant reaction mixture was poured into ice-cooled water and extracted with dichloromethane. The organic layer was washed with water and dried over anhydrous magnesium sulfate. After evaporation of the solvent, the residue was purified by silica gel column chromatography- using n-hexane to obtain 2.16 g of an oily product of 2-methylthio-4'-(trifluoromethyl)propiophenone (yield: 40.8%).

NMR(CDCl$_3$)δ: 1.55(d, 3H), 1.94(s, 3H), 4.30(q, 1H), 7.72(d, 2H), 8.11(d, 2H)

Reference Example 3

To 2.02 g of 2-methylthio-4'-(trifluoromethyl)propiophenone dissolved in 20 ml of tetrahydrofuran was added under ice-cooling 0.33 g of a 60% aqueous solution of sodium hydride, and the mixture was reacted at room temperature with stirring until no bubbles were produced. After an addition of 1.27 g of methyl iodide, the mixture was stirred at room temperature for a further 2 hours. The resultant reaction mixture was poured into ice-cooled water and extracted with dichloromethane. The organic layer was washed with water and dried over anhydrous magnesium sulfate. After evaporation of the solvent, the residue was purified by silica gel column chromatography using n-hexane to obtain 1.27 g of an oily product of 2-methylthio-4'-(trifluoromethyl)isobutyrophenone (yield: 59.5%).

NMR(CDCl$_3$)δ: 1.54(s, 6H), 2.01(s, 3H), 7.66(d, 2H), 8.11(d, 2H)

Reference Example 4

To a tetrahydrofuran solution of Grignard reagent prepared from 5.35 g of magnesium and 24.6 g of isopropyl bromide was added under ice-cooling 17.4 g of 4-(trifluoromethyl)benzaldehyde dissolved in tetrahydrofuran, and the mixture was stirred for 30 minutes. The resultant reaction mixture was treated with a saturated NH$_4$Cl aqueous solution and extracted with ether. The organic layer was washed with water and dried over anhydrous magnesium sulfate. After evaporation of the solvent, the residue was purified by silica gel column chromatography using n-hexane/dichloromethane to obtain 8.02 g of an oily product of 1-(trifluoromethyl)phenyl-2-methylpropane-1-ol (yield: 36.8%).

NMR(CDCl$_3$)δ: 0.84, 0.96(d, 3H for each), 1.7–2.1 (m, 1H), 4.47(d, 1H), 7.43, 7.58(d, 2H for each)

Reference Example 5

To 8 g of 1-(trifluoromethyl)phenyl-2-methylpropane-1-ol dissolved in dichloromethane was added 15.8 g of pyridinium chlorochromate, and the mixture was stirred at room temperature for 3 hours. After separating the deposited undissolvable substance by filtration, the filtrate was concentrated and the residue was purified by silica gel column chromatography to obtain 7.9 g of an oily product of 4-(trifluoromethyl)iscbutyrophenone (yield: 100%).

NMR(CDCl$_3$)δ: 1.24(d, 6H), 3.4–3.7(m, 1H), 7.71, 8.04 (d, 2H for each)

Reference Example 6

To 1 g of 4-(trifluoromethyl)isobutyrophenone dissolved in acetic acid was added 0.81 g of bromine at 40° C., and the mixture was stirred for 3 hours. The reaction mixture was poured into ice-cooled water and extracted with ether. The organic layer was washed with a 5% sodium bicarbonate aqueous solution and then with water, dried over anhydrous magnesium sulfate, and the solvent was evaporated to obtain 1.36 g of an oily product of 2-bromo-4'-(trifluoromethyl)-isobutyrophenone (yield: 100%).

NMR(CDCl$_3$)δ: 2.03(s, 6H), 7.71, 8.19(d, 2H for each)

Reference Example 7

To 1 g of 2-bromo-4'-(trifluoromethyl)isobutyrophenone dissolved in methanol was added under ice-cooling 1.74 g of 15% solution of methyl mercaptan sodium salt, and the mixture was stirred for 30 minutes. The reaction mixture was poured into ice-cooled water and extracted with dichloromethane. The organic layer was washed with water, dried over anhydrous magnesium sulfate, and the solvent was evaporated. The residue was purified by silica gel column chromatography using n-hexane/dichloromethane to obtain 0.61 g of an oily product of 2-methylthio-4'-(trifluoromethyl)isobutyrophenone (yield: 68.7%).

NMR(CDCl$_3$)δ: 1.54(s, 6H), 2.01(s, 3H), 7.66, 8.11 (d, 2H)

EXAMPLE 1

Into 50 ml of t-butanol were dissolved 4.97 g of 2-methylthio-4'-(trifluoromethyl)propiophenone, 8.05 g of trimethylsulfoxonium iodide, 5.6 g of potassium hydroxide, and 3.18 g of 1,2,4-triazole, and the mixture was stirred at 80° C. for 7 hours. After the reaction, the solvent was evaporated, water was added to the residue, and the mixture was extracted with chloroform. The organic layer was washed with water, dried over anhydrous magnesium sulfate, and the solvent was evaporated. The residue was purified by silica gel column chromatography using n-hexane to obtain first 0.64 g of A isomer of 3-methylthio-1-(1,2,4-triazol-1-yl)-2-[(4-trifluoromethyl)phenyl]butane-2-ol (Compound No. 1) (yield: 9.6%), and then 0.06 g of B isomer (Compound No. 2) (yield: 0.9%).

EXAMPLE 2

To a solution of 0.35 g (1.06×10$^{-3}$ mole) of 3-methylthio-1-(1,2,4-triazol-1-yl-2-[(4-trifluoromethyl)-phenyl]butane-2-ol (Compound No. 1) in 10 ml of chloroform was added under ice-cooling 0.23 g (1.06×10$^{-3}$ mole) of m-chloroperbenzoic acid, and the mixture was stirred at 0° to 10° C. for 0.5 hour. The reaction mixture thus obtained was washed with 10% potassium carbonate aqueous solution and then with water, dried over anhydrous magnesium sulfate, and the solvent was evaporated. The residue was purified by silica gel column chromatography using dichloromethane to obtain first 0.23 g of a isomer of 3-methylsulfinyl-1-(1,2,4-triazol-1-yl)-2-[(4-trifluoromethyl)phenyl]butane-2-ol (Compound No. 3) (yield: 62.7%) and subsequently 0.137 g of b isomer (Compound No. 4) (yield: 37.3%).

EXAMPLE 3

0.30 g ($9.1 \times 10^{-4}$ mole) of 3-methylthio-1-(1,2,4-triazol-1-yl)-2-[(4-trifluoromethyl)phenyl]butane-2-ol (Compound No. 1) was dissolved in 30 ml of chloroform. To the solution was added 0.586 g ($2.72 \times 10^{-3}$ mole) of m-chloroperbenzoic acid, a bit at a time at room temperature, and the mixture was stirred for 2 hours. The reaction mixture thus obtained was washed with 10% potassium carbonate aqueous solution and then with water, dried over anhydrous magnesium sulfate, and the solvent was evaporated. The residue was purified by silica gel column chromatography using dichloromethane to obtain 0.33 g of 3-methylsulfonyl-(1,2,4-triazol-1-yl)-2-[(4-trifluoromethyl)phenyl]-butane-2-ol (Compound No. 5) (yield: 100%).

EXAMPLE 4

An oily product of 3-methylsulfonyl-1-(1,2,4-triazol-1-yl)-2-[(4-trifluoromethyl)phenyl]butane-2-ol (Compound No. was prepared by the reaction similar to the reaction of Example 3 from 3-methylthio-1-(1,2,4-triazol-1-yl)-2-[(4-trifluoromethyl)phenyl]butane-2-ol (Compound No. 2).

EXAMPLE 5

Into 10 ml of t-butanol were dissolved 1.22 g of 2-methylthio-4'-(trifluoromethyl)isobutyrophenone, 1.36 g of trimethylsulfoxonium iodide, 1.07 g of potassium hydroxide, and 0.74 g of 1,2,4-triazole, and the mixture was stirred at 80° C. for 6 hours. After the reaction, the solvent was evaporated, water was added to the residue, and the mixture was extracted with chloroform. The organic layer was washed with water, dried over anhydrous magnesium sulfate, and the solvent was evaporated. The residue was purified by silica gel column chromatography using dichloromethane to obtain 0.66 g of an oily product of 3-methyl-3-methylthio-1-(1,2,4-triazol-1-yl)-2-[(4-trifluoromethyl)phenyl]butane-2-ol (Compound No. 7) (yield: 41.1%).

EXAMPLE 6

To a solution of 0.37 g ($1.07 \times 10^{-3}$ mole) of 3-methyl-3-methylthio-1-(1,2,4-triazol-1-yl)-2-[(4-trifluoromethyl)phenyl]butane-2-ol (Compound No. 7) in 10 ml of chloroform was added under ice-cooling 0.231 g ($1.07 \times 10^{-3}$ mole) of m-chloroperbenzoic acid, and the mixture was stirred at 0° to 10° C. for 20 minutes. The reaction mixture thus obtained was washed with 10% potassium carbonate aqueous solution and then with water, dried over anhydrous magnesium sulfate, and the solvent was evaporated. The residue was purified by silica gel column chromatography using dichloromethane to obtain first 0.125 g of a isomer of 3-methyl-3-methylsulfinyl-1-(1,2,4-triazol-1-yl)-2-[(4-trifluoromethyl)phenyl]-butane-2-ol (Compound No. 8) (yield: 32.3%), and then 0.155 g of b isomer (Compound No. 9) (yield: 40.0%).

EXAMPLE 7

0.36 g ($1.04 \times 10^{-3}$ mole) of 3-methyl-3-methylthio-1-(1,2,4-triazol-1-yl)-2-[(4-trifluoromethyl)phenyl]butane-2-ol (Compound No. 7) was dissolved in 40 ml of chloroform. To the solution was added 0.68 g ($3.13 \times 10^{-3}$ mole) of m-chloroperbenzoic acid a bit at a time at room temperature, and the mixture was stirred for 14 hours. The reaction mixture thus obtained was washed with 10% potassium carbonate aqueous solution and then with water, dried over anhydrous magnesium sulfate, and the solvent was evaporated. The residue was purified by silica gel column chromatography using dichloromethane to obtain 3.36 g of 3-methyl-3-methylsulfonyl-1-(1,2,4-triazol-1-yl)-2-[(4-trifluoromethyl)phenyl]-butane-2-ol (Compound No. 10) (yield: 91.5%).

EXAMPLE 8

The following Compounds No. 11-15 were prepared in the same manner as in Examples 1-7.

Compound 11

3-Methylsulfonyl-1-(1,2,4-triazol-1-yl)-2-[(4-trifluoromethyl)phenyl]pentane-2-ol

Compound 12

3-Ethylsulfonyl-3-methyl-1-(1,2,4-triazol-1-yl]-2-[(4-trifluoromethyl)phenyl]butane-2-ol

Compound 13

3-t-Butylsulfonyl-1-(1,2,4-triazol-1-yl)-2-[(4-trifluoromethyl)phenyl]butane-2-ol (a isomer)

Compound 14

3-t-Butylsulfonyl-1-(1,2,4-triazol-1-yl)-2-[(4-trifluoromethyl)phenyl]butane-2-ol (b isomer)

Compound 15

1-[1-(1-methylsulfonyl)cyclopropyl]-2-(1,2,4-triazol-1-yl)-1-[(4-trifluoromethyl)phenyl]ethane-1-ol

Reference Example 8

A mixture of 9.46 g ($6.15 \times 10^{-2}$ mole) of S(−)methyl-p-tolyl sulfoxide and 100 ml of tetrahydrofuran was added dropwise to 53.3 ml of a cyclohexane solution of lithium diisopropylamide (1.5 mole/l; $7.99 \times 10^{-2}$ mole) at 5° C. and the mixture was stirred at room temperature for 2 hours. To this solution was dropwise added at 10° C. 16.1 g ($6.15 \times 10^{-2}$ mole) of 2-methylthio-4'-(trifluoromethyl)isobutyrophenone and the mixture was stirred at room temperature for a further 2 hours. After evaporating the solvent, an oil obtained was treated with 100 ml of saturated $NH_4Cl$ aqueous solution and extracted with ethyl acetate. The organic layer was washed with water, dried over anhydrous magnesium sulfate, and the solvent was evaporated. The residue was submitted to silica gel column chromatography using n-hexane/ethyl acetate to separate two diastereomers (IV-1) and (IV-2) of (−)-α-(1-methyl-1-methylthio)ethyl-α-(4-methylbenzosulfinyl)methyl-4-(trifluoromethyl)benzyl alcohol.

Diastereomer (IV-1)

Amount: 11.19 g (yield: 43.8%), an oily substance
$[\alpha]_D^{25} = -64.2°$ (acetone, c=0.5)
IR: $\nu cm^{-1}$ 1325, 1065
NMR(CDCl$_3$)δ ppm: 1.17, 1.31(s, 3H for each), 1.93(s, 3H), 2.43(s, 3H), 3.64(s, 2H), 7.2-8.0(m, 8H)

Diastereomer (IV-2)

Amount: 10.35 g (yield: 40.5%), an oily substance
$[\alpha]_D^{25} = -131.2°$ (acetone, c=0.5)
IR: $\nu$ cm$^{-1}$ 1330, 1065
NMR(CDCl$_3$)δ ppm: 1.17, 1.24(s, 3H for each), 2.04(s, 3H), 2.36(s, 3H), 3.50, 4.17(d, 1H for each), 7.0-7.7(m, 8H)

Reference Example 9

11.19 g ($2.69 \times 10^{-2}$ mole) of diastereomer (IV-1) produced in Reference Example 8 was dissolved in 100 ml of dichloromethane. To the mixture was added under ice-cooling 11.6 g ($5.38 \times 10^{-2}$ mole) of 80% m-chloroperbenzoic acid, and the mixture was stirred at 0°–10° C. for 1 hour. The reaction mixture thus obtained was washed with 20% sodium hydroxide aqueous solution and then with water, dried over anhydrous magnesium sulfate, and the solvent was evaporated. The residue was purified by silica gel column chromatography using chloroform to obtain 10.20 g of crystals of (−)-α-(1-methyl-1-methylsulfonyl)ethyl-α-(4-methylbenzosulfinyl)-methyl-4-(trifluoromethyl)benzyl alcohol (V) (yield: 84.6%).

m.p. 100°–102° C.
$[\alpha]_D^{25} = -35.6°$ (acetone, c=0.5)
IR: $\nu\text{cm}^{-1}$ 1330, 1120, 1065
NMR(CDCl$_3$)δ ppm: 1.18, 1.39(s, 3H for each), 2.43(s, 3H), 3.18(s, 3H), 3.51, 4.34(d, 1H for each), 7.0–8.2(m, 8H)

Reference Example 10

10.20 g ($2.28 \times 10^{-2}$ mole) of (−)-α-(1-methyl-1-methylsulfonyl)ethyl-α-(4-methylbenzosulfinyl)methyl-4-(trifluoromethyl)benzyl alcohol (V) was dissolved in 50 ml of acetone. To the mixture was added dropwise under ice-cooling 5.36 g ($6.83 \times 10^{-2}$ mole) of acetyl chloride and further added 10.25 g ($6.83 \times 10^{-2}$ mole) of sodium iodide, following which the mixture was stirred at 0°–10° C. for 1 hour. After the solvent was evaporated, the residue was extracted with ether. The organic layer was washed with water, dried over anhydrous magnesium sulfate, and concentrated. The residue was purified by silica gel column chromatography using n-hexane to obtain 8.93 g of crystals of (+)-α-(1-methyl-1-methylsulfonylethyl-α-[(4-methylphenyl)thio]-methyl-4-(trifluoromethyl)benzyl alcohol (VI) (yield: 90.8%).

m.p. 111°–113° C.
$[\alpha]_D^{25} = +5.8°$ (acetone, c=0.5)
IR:$\nu\text{cm}^{-1}$ 1330, 1110
NMR(CDCl$_3$)δ ppm: 1.19, 1.46(s, 3H for each), 2.26(s, 3H), 3.10(s, 3H), 4.02, 4.40(d, 1H for each), 6.9–7.2 (m, 4H), 7.4–7.6(m, 4H)

Reference Example 11

8.93 g ($2.07 \times 10^{-2}$ mole) of (+)-α-(1-methyl-1-methylsulfonyl)ethyl-α-[(4-methylphenyl)-thio]methyl-4-(trifluoromethyl)benzyl alcohol (VI) was dissolved in 50 ml of dichloromethane, and to the mixture was added dropwise under ice-cooling 100 ml of a dichloromethane solution of triethyloxonium tetrafluoroborate (1 mole/l; 0.1 mole), followed by stirring at room temperature overnight. After an addition of 40 ml of 20% sodium hydroxide aqueous solution under ice-cooling, the mixture was stirred at room temperature for a further 1 hour. The organic layer was separated, washed with water, dried over anhydrous magnesium sulfate, and the solvent was evaporated. The residue was purified by silica gel column chromatography using n-hexane to obtain 5.45 g of an oily product of (−)-2-(1-methyl-1-methylsulfonyl)ethyl-2-[(4-(trifluoromethyl)phenyl]oxylane (VII) (yield: 85.6%).

$[\alpha]_D^{25} = -20.6°$ (acetone, c=0.5)
IR: cm$^{-1}$ 1325, 1110
NMR(CDCl$_3$)δ ppm: 1.47, 1.52(s, 3H for each), 2.81, 3.62 (d, 1H for each), 2.89(s, 3H], 7.61(s, 4H)

EXAMPLE 9

1.50 g ($4.87 \times 10^{-3}$ mole) of (−)-2-(1-methyl-1-methylsulfonyl)ethyl-2-[(4-(trifluoromethyl)phenyl]oxylane (VII) and 1.73 g ($2.5 \times 10^{-2}$ mole) of triazole were dissolved in 45 ml of dimethylformamide. To this solution was added 0.69 g ($5.0 \times 10^{-3}$ mole) of potassium carbonate and the mixture was stirred at room temperature overnight. The resultant mixture was dissolved in a water/ether mixture. The organic layer was separated, washed with water, dried over anhydrous magnesium sulfate, and the solvent was evaporated. The residue was purified by silica gel column chromatography using chloroform. 1.198 g of crystals of (−)-3-methyl-3-methylsulfonyl-1-(1,2,4-triazol-1-yl)-2-[(4-trifluoromethyl)phenyl]butane-2-ol (Compound No. 16) was obtained by recrystallization from an isopropylether/diethylether mixed solvent (yield: 54.2%).

$[\alpha]_D^{25} = -9.6°$ (acetone, c=0.25)

Characteristics, IR, and NMR of compounds prepared in Examples 1–9 are shown in Table 2.

TABLE 2

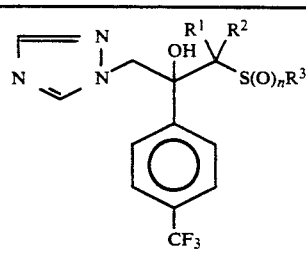

| Compound No. | R$_1$ | R$_2$ | R$_3$ | n | Characteristics m.p. (°C.) | IR ($\nu\text{cm}^{-1}$) | NMR (CDCl$_3$) δ (ppm) |
|---|---|---|---|---|---|---|---|
| 1 | CH$_3$ | H | CH$_3$ | 0 | White crystals 97–100 | 3150, 1330 | 1.21(d, 3H), 2.16(s, 3H), 3.02(q, 1H), 4.63, 5.00(d, 1H for each), 7.42, 7.54(d, 2H for each), 7.81(s, 2H) |
| 2 | CH$_3$ | H | CH$_3$ | 0 | Oil | 3220, 1325 | 1.28(d, 3H), 1.93(s, 3H), 2.84(q, 1H), 4.80, 4.87(d, 1H for each), 7.60(s, 4H), 7.88, 8.28(s, 1H for each) |
| 3 | CH$_3$ | H | CH$_3$ | 1 | White crystals 147–150 | 3180, 1325 | 1.20(d, 3H), 2.64(s, 3H), 2.96(q, 1H), 4.52, 5.09(d, 1H for each), 7.64(s, 4H), 7.94, 8.26(s, 1H for each) |
| 4 | CH$_3$ | H | CH$_3$ | 1 | White crystals 168–169 | 3200, 1325 | 1.21(d, 3H), 2.66(s, 3H), 3.28(q, 1H) 4.80, 5.04(d, 1H for each), 7.36, 7.60(d, 2H for each), 7.94, 8.36(s, 1H for each) |
| 5 | CH$_3$ | H | CH$_3$ | 2 | White crystals 172–175 | 3350, 1320 | 1.30(d, 3H), 3.06(s, 3H), 3.38(q, 1H), 5.26, 5.39(d, 1H for each), 7.44, 7.58(d, 2H for each), |

TABLE 2-continued

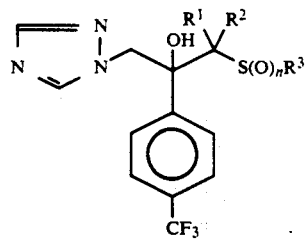

| Compound No. | R₁ | R₂ | R₃ | n | Characteristics m.p. (°C.) | IR (νcm⁻¹) | NMR (CDCl₃) δ (ppm) |
|---|---|---|---|---|---|---|---|
| 6 | CH₃ | H | CH₃ | 2 | Oil | 3400, 1320 | 7.71, 7.80(s, 1H for each) 1.54(d, 3H), 2.80(s, 3H), 3.2-3.6(m, 1H), 4.90, 5.10(d, 1H for each), 7.59(s, 4H), 7.77, 8.13(s, 1H for each) |
| 7 | CH₃ | CH₃ | CH₃ | 0 | Oil | 3400, 1320 | 1.31, 1.38(s, 3H for each), 2.02(s, 3H), 4.88, 5.14(d, 1H for each), 7.50, 7.64(d, 2H for each), 7.71, 7.99(s, 1H for each) |
| 8 | CH₃ | CH₃ | CH₃ | 1 | White crystals 159-162 | 3300, 1325 | 1.05, 1.55(s, 3H for each), 2.49(s, 3H), 4.76, 5.56(d, 1H for each), 7.54, 7.68(d, 2H for each), 7.73, 8.15(s, 1H for each) |
| 9 | CH₃ | CH₃ | CH₃ | 1 | White crystals 82-85 | 3250, 1330 | 1.07, 1.47(s, 3H for each), 2.59(s, 3H), 5.04(s, 2H), 7.58(s, 4H), 7.74, 8.21(s, 1H for each) |
| 10 | CH₃ | CH₃ | CH₃ | 2 | White crystals 156-157 | 3150, 1325 | 1.27, 1.53(s, 3H for each), 3.21(s, 3H), 4.96, 5.20(d, 1H for each), 7.4-7.7(m, 4H), 7.69, 7.96(s, 1H for each) |
| 11 | C₂H₅ | H | CH₃ | 2 | Oil | 3400, 1320 | 0.74(t, 3H), 0.8-2.0(m, 3H), 3.10(s, 3H), 4.83, 5.30(d, 1H for each), 7.4-8.0(m, 6H), |
| 12 | CH₃ | CH₃ | C₂H₅ | 2 | White crystals 169-170 | 3150, 1325 | 1.27, 1.54(s, 3H for each), 1.49(t, 3H), 3.1-3.8(m, 2H), 5.17, 5.43(d, 1H for each), 7.4-7.8(m, 4H), 7.66, 7.99(s, 1H for each) |
| 13 | CH₃ | H | t-C₄H₉ | 2 | White crystals 152-153 | 3350, 1320 | 1.35(s, 9H), 1.59(d, 3H), 3.60(q, 1H), 4.55, 4.99(d, 1H for each), 7.62(s, 4H), 7.91, 8.27(s, 1H for each) |
| 14 | CH₃ | H | t-C₄H₉ | 2 | White crystals 211-212 | 3400, 1320 | 1.35(s, 9H), 1.36(d, 3H), 3.50(q, 1H), 4.78, 5.23(d, 1H for each), 7.61, 7.74(d, 2H for each), 7.87, 8.21(s, 1H for each) |
| 15 | —CH₂CH₂— | | CH₃ | 2 | White crystals 164-165 | 3200, 1320 | 0.7-1.6(m, 4H), 2.25(s, 3H), 5.34(s, 2H), 7.65, 7.74(d, 2H for each), 7.91, 8.53 (s, 1H for each) |
| 16 | CH₃ | CH₃ | CH₃ | 2 | White crystals 97-98 | 1330, 1110 | 1.26, 1.53(s, 3H for each), 3.21(s, 3H), 5.13, 5.47(d, 1H for each), 7.4-7.8(m, 4H), 7.67, 7.99(s, 1H for each) |

Obviously, numerous modifications and variations of the present invention are possible in light of the above teachings. It is therefore to be understood that within the scope of the appended claims, the invention may be practiced otherwise than as specifically described herein.

What is claimed is:

1. A triazole derivative of formula (I),

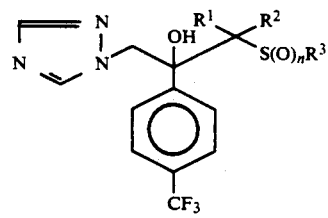

wherein $R^1$ and $R^2$ represent a hydrogen atom or a lower alkyl group, or $R^1$ and $R^2$ together form a lower alkylene group, $R^3$ represents methyl, and n denotes an integer of 0 to 2, provided that $R^1$ and $R^2$ are not both a hydrogen atom at the same time, and a salt thereof.

2. A composition for treating mycoses comprising an effective amount of a triazole derivative or a salt thereof according to claim 1 and a pharmaceutically acceptable carrier.

* * * * *